United States Patent
Kojima et al.

(10) Patent No.: US 7,145,048 B2
(45) Date of Patent: Dec. 5, 2006

(54) PROCESS FOR PRODUCING ADAMANTANE OR ANALOGUE

(75) Inventors: Akio Kojima, Yamaguchi (JP); Masao Saito, Yamaguchi (JP)

(73) Assignee: Idemitsu Kosan Co., Ltd., Tokyo (JP)

( * ) Notice: Subject to any disclaimer, the term of this patent is extended or adjusted under 35 U.S.C. 154(b) by 405 days.

(21) Appl. No.: 10/480,463

(22) PCT Filed: Jun. 12, 2002

(86) PCT No.: PCT/JP02/05868

§ 371 (c)(1),
(2), (4) Date: Dec. 12, 2003

(87) PCT Pub. No.: WO02/102747

PCT Pub. Date: Dec. 27, 2002

(65) Prior Publication Data

US 2004/0171902 A1    Sep. 2, 2004

(30) Foreign Application Priority Data

Jun. 13, 2001    (JP) .............................. 2001-179178

(51) Int. Cl.
*C07C 13/28* (2006.01)
(52) U.S. Cl. ..................................... 585/352
(58) Field of Classification Search ................ 585/352
See application file for complete search history.

(56) References Cited

U.S. PATENT DOCUMENTS

| | | | | |
|---|---|---|---|---|
| 3,457,317 A | * | 7/1969 | Hoffmann et al. ........... 585/352 |
| 3,944,626 A | * | 3/1976 | Honna et al. ................ 585/352 |
| 6,784,328 B1 | * | 8/2004 | Kojima et al. ................ 585/21 |
| 2003/0023122 A1 | * | 1/2003 | Kojima et al. .............. 585/351 |

FOREIGN PATENT DOCUMENTS

| | | |
|---|---|---|
| JP | 60-246333 | 12/1985 |
| JP | 4-202143 | 7/1992 |

OTHER PUBLICATIONS

U.S. Appl. No. 10/942,098, filed Sep. 16, 2004, Kojima et al., ABN.
U.S. Appl. No. 10/182,705, filed Aug. 7, 2002, Kojima et al.
U.S. Appl. No. 10/181,968, filed Aug. 6, 2002, Kojima et al., ABN.
U.S. Appl. No. 10/363,406, filed Mar. 4, 2003, Kojima et al.

* cited by examiner

*Primary Examiner*—Thuan Dinh Dang
(74) *Attorney, Agent, or Firm*—Oblon, Spivak, McClelland, Maier & Neustadt, P.C.

(57) ABSTRACT

The invention relates to a method of selectively producing adamantanes in a production apparatus made of an inexpensive material, not having any negative influence on the natural environment. The method for producing adamantanes includes isomerizing a tricyclic saturated hydrocarbon having at least 10 carbon atoms in the presence of a metal-carrying solid acid catalyst, wherein water and/or alcohol is made to coexist along with the catalyst during the isomerization.

14 Claims, No Drawings

US 7,145,048 B2

PROCESS FOR PRODUCING ADAMANTANE OR ANALOGUE

TECHNICAL FIELD

The present invention relates to a method for producing adamantanes. More precisely, the invention relates to a method of selectively producing adamantanes in a production apparatus made of an inexpensive material, not having any negative influence on the natural environment.

BACKGROUND ART

Adamantanes are useful for intermediates of various chemicals such as lubricants and medicines. For producing such adamantanes, generally employed is a method of isomerizing tricyclic saturated hydrocarbons having at least 10 carbon atoms each. For the isomerization, used is aluminium chloride for the catalyst.

However, in the method of using aluminium chloride for the catalyst for the isomerization, a large amount of aluminium chloride must be used relative to the starting compound. In addition, in the method, the aluminium chloride catalyst forms a complex with a heavy component during the isomerization, and therefore it cannot be recycled. Accordingly, the method gives a large amount of aluminium waste and its serious problem is that the aluminium waste to be processed for its disposal has some negative influence on the natural environment. Another problem with the method is that the aluminium chloride catalyst used discolors the adamantanes produced therein, and therefore the method requires recrystallization of the products or decoloration thereof with activated charcoal, but the post-treatment is troublesome.

In JP-B 52-2909 and 53-35944, proposed is a method of using a catalyst of various active metals such as platinum, rhenium, nickel or cobalt carried by cation-exchanged zeolite, for that isomerization. In the method, however, since the yield of adamantanes produced through isomerization using the metal-carrying catalyst is low, hydrogen chloride is used along therewith for increasing the yield of the adamantanes. Therefore, there is disadvantage in that a production apparatus made of an expensive corrosion-resistant material must be used in this method.

Given that situation, it is desired to develop a method of selectively producing adamantanes in a production apparatus made of an inexpensive material, not having any negative influence on the natural environment.

The object of the present invention is to provide a method of selectively producing adamantanes in a production apparatus made of an inexpensive material, not having any negative influence on the natural environment.

DISCLOSURE OF THE INVENTION

We, the present inventors have assiduously studied so as to solve the problems noted above, and, as a result, have found that, in a method for producing adamantanes by isomerizing a tricyclic saturated hydrocarbon having at least 10 carbon atoms in the presence of a metal-carrying solid acid catalyst, when water and/or alcohol is made to coexist along with the catalyst during the isomerization, then it attains the object as above. On the basis of this finding, we have completed the present invention.

Specifically, the invention is summarized as follows:

(1) A method for producing adamantanes by isomerizing a tricyclic saturated hydrocarbon having at least 10 carbon atoms in the presence of a metal-carrying solid acid catalyst, wherein water and/or alcohol is made to coexist along with the catalyst during the isomerization.

(2) The method for producing adamantanes of above (1), wherein the metal in the metal-carrying solid acid catalyst is a metal of the Groups 8 to 10 of the Periodic Table.

(3) The method for producing adamantanes of above (2), wherein the metal of the Groups 8 to 10 of the Periodic Table is platinum.

(4) The method for producing adamantanes of any of above (1) to (3), wherein the metal-carrying solid acid catalyst is a catalyst of a metal of the Groups 8 to 10 of the Periodic Table carried by zeolite.

(5) The method for producing adamantanes of any of above (1) to (4), wherein the metal-carrying solid acid catalyst is a solid acid catalyst of platinum carried by Y-type zeolite.

(6) The method for producing adamantanes of any of above (1) to (5), wherein an unsaturated bond-having compound is made to further coexist along with the catalyst during the isomerization.

(7) The method for producing adamantanes of any of above (1) to (5), wherein a monocyclic saturated hydrocarbon is made to further coexist along with the catalyst during the isomerization.

(8) The method for producing adamantanes of any of above (1) to (5), wherein both an unsaturated bond-having compound and a monocyclic saturated hydrocarbon are made to further coexist along with the catalyst during the isomerization.

BEST MODES OF CARRYING OUT THE INVENTION

Embodiments of the invention are described hereinunder.

The invention is a method for producing adamantanes by isomerizing a tricyclic saturated hydrocarbon having at least 10 carbon atoms in the presence of a metal-carrying solid acid catalyst, wherein water and/or alcohol is made to coexist along with the catalyst during the isomerization. The adamantanes to be produced in the invention are hydrocarbons having an adamantane structure, including unsubstituted adamantane and alkyl-substituted adamantanes having a lower alkyl group such as methyl or ethyl group.

The tricyclic saturated hydrocarbon having at least 10 carbon atoms, which is the stating material in the invention, is especially preferably a tricyclic saturated hydrocarbon having from 10 to 15 carbon atoms, including, for example, trimethylenenorbornane [tetrahydrodicyclopentadiene], perhydroacenaphthene, perhydrofluoren, perhydrophenalene, 1,2-cyclopentanperhydronaphthalene, perhydroanthracene, perhydrophenanthrene. Also preferred for use herein are alkyl-substituted derivatives of these compounds, for example, 9-methylperhydroanthracene.

These tricyclic saturated hydrocarbons having at least 10 carbon atoms each can be readily obtained by hydrogenating starting compounds such as dicyclopentadiene or acenaphthene in the presence of a known hydrogenation catalyst such as Raney nickel or platinum.

The catalyst to be used in the invention is a metal-carrying solid acid catalyst having at least one type of metal. Preferred examples of the metal in the metal-carrying solid acid catalyst are metals of Groups 8 to 10 of the Periodic Table, concretely iron, cobalt, nickel, ruthenium, rhodium, palladium, osmium, iridium, and platinum. Of those metals, more preferred is a solid acid catalyst with platinum. Preferred examples of the solid acid that carries the metal are various types of zeolite such as A-type zeolite, L-type zeolite, X-type zeolite, Y-type zeolite, ZSM-5; and metal oxides such as silica-alumina, alumina, heteropoly-acids. Of those solid acids, more preferred are X-type zeolite and Y-type zeolite.

For producing the metal-carrying solid acid catalyst with a carrier of zeolite, for example, at least one type of metal is applied to zeolite through ion-exchanging or dipping. For producing it through ion-exchanging, for example, an aqueous solution of a salt or complex of the metal is kept in contact with zeolite so as to exchange the cation site (e.g., $H^+$, $NH_4^+$) in zeolite with the metal, and the thus-processed zeolite is dried and baked. For producing the catalyst through dipping, for example, an aqueous solution of a salt or complex of the metal is mixed with zeolite, and then the resulting mixture is dried up in a rotary evaporator or the like whereby the metal is infiltrated into the carrier, zeolite. Regarding its morphology, the catalyst thus obtained may be powdery or granular.

In the method of the invention, a tricyclic saturated hydrocarbon having at least 10 carbon atoms is isomerized in the presence of the metal-carrying solid acid catalyst that is prepared in the manner as above, and the isomerization is effected in the co-existence of water and/or alcohol. The alcohol includes, for example, monoalcohols such as methyl alcohol, isopropyl alcohol, tert-butyl alcohol, benzyl alcohol; and polyalcohols such as ethylene glycol, glycerin.

The ratio of the coexisting water and/or alcohol to the starting compound, tricyclic saturated hydrocarbon to be isomerized preferably falls between 1:10000 and 2:1 by mass. The reason is because, if the ratio of the coexisting water and/or alcohol to the starting compound is smaller than 1:10000, the selectivity of adamantanes in the reaction product could not increase; and if it is larger than 2:1, the reactivity of the starting compound will lower. More preferably, the ratio of the coexisting water and/or alcohol to the starting compound, tricyclic saturated hydrocarbon falls between 1:1000 and 1:1.

In the method of the invention of isomerizing a tricyclic saturated hydrocarbon having at least 10 carbon atoms in the presence of a metal-carrying solid acid catalyst, the selectivity of adamantanes is more increased when an unsaturated bond-having compound is made to further coexist along with the component, water and/or alcohol. The unsaturated compound includes, for example, aromatic hydrocarbons such as benzene, toluene, xylene, naphthalene, anthracene; oxygen-containing aromatic compounds such as phenol, benzaldehyde, benzoic acid; nitrogen-containing aromatic compounds such as aniline, nitrobenzene; halogen-containing aromatic compounds such as chlorobenzene, bromobenzene; alicyclic unsaturated hydrocarbons such as cyclopentadiene, dicyclopentadiene, cyclohexene, norbornene; acyclic unsaturated hydrocarbons such as propylene, butene, butadiene, pentene.

The ratio of the unsaturated compound to the starting compound, tricyclic saturated hydrocarbon may fall between 1:1000 and 2:1 by mass. The reason is because, if the ratio of the unsaturated compound to the starting compound, tricyclic saturated hydrocarbon is smaller than 1:1000 by mass, the selectivity of adamantanes in the reaction product could not increase; and if it is larger than 2:1, the reactivity of the starting compound will lower.

In the method of the invention of isomerizing a tricyclic saturated hydrocarbon having at least 10 carbon atoms in the presence of a metal-carrying solid acid catalyst, adding water and/or alcohol to the isomerization system increases the selectivity of adamantanes but it lowers in some degree the conversion of the starting compound. To solve the problem, a monocyclic saturated hydrocarbon is made to further coexist in the isomerization system along with the component, water and/or alcohol whereby the conversion of the starting compound tricyclic saturated hydrocarbon can be increased. The monocyclic saturated hydrocarbon includes, for example, methylcyclopentane, ethylcyclopentane, methylcyclohexane, ethylcyclohexane, dimethylcyclopentane, and dimethylcyclohexane.

The ratio of the monocyclic saturated hydrocarbon to the starting compound, tricyclic saturated hydrocarbon may fall between 1:50 and 100:1 by mass. The reason is because, if the ratio of the monocyclic saturated hydrocarbon to the starting compound, tricyclic saturated hydrocarbon is smaller than 1:50 by mass, the conversion of the tricyclic saturated hydrocarbon could not increase; and if it is larger than 100:1 by mass, the reactivity will lower.

In the method of the invention of isomerizing a tricyclic saturated hydrocarbon having at least 10 carbon atoms in the presence of a metal-carrying solid acid catalyst, the yield of adamantanes is more increased when the above-mentioned, unsaturated bond-having compound and monocyclic saturated hydrocarbon are made to both coexist along with the component, water and/or alcohol in isomerizing the starting compound.

Next described is the reaction condition in isomerization of the tricyclic saturated hydrocarbon having at least 10 carbon atoms in the presence of the metal-carrying solid acid catalyst along with water and/or alcohol. The reaction temperature may fall between 150 and 500° C., but preferably between 200 and 400° C.; and the reaction pressure may be normal pressure or increased pressure. Regarding the reaction style, employable are any of flow reactors or batch reactors. In case where the reaction is effected in a batch reactor, the reaction time may fall between 1 and 50 hours. Preferably, the reaction is effected in the presence of hydrogen for improving the yield of the product, adamantanes. For regenerating the catalyst used in the reaction, employable is a method of reactivating the used catalyst by baking it in air at a temperature falling between 350 and 550° C.

The invention is described more concretely with reference to the following Examples and Comparative Examples.

EXAMPLE 1

(1) Preparation of Metal-Carrying Solid Acid Catalyst:

235 g of powder of sodium ion-exchanged Y-type zeolite was put into 2000 g of pure water and stirred to give a suspension slurry, to which was added dilute nitric acid to thereby make the resulting slurry have a pH of 5.5. With stirring the suspension slurry, a solution of 246 g of lanthanum nitrate hexahydrate [$La(NO_3)_2 \cdot 6H_2O$] dissolved in 500 g of warm water was gradually added thereto, and the resulting mixture was heated at 90° C., stirred for 30 minutes, then filtered and washed. The resulting solid was dried at 110° C. overnight, then ground and baked in air at 600° C. for 3 hours.

Next, the thus-baked powder was put into 2000 g of pure water and stirred. To the resulting suspension, added was 228 g of ammonium sulfate, stirred at 95° C. for 30 minutes, then filtered and washed. The ion-exchanging process was repeated once again, and the product finally filtered and washed was dried overnight at 110° C.

Next, the product that had been filtered and washed in the above was ground, and then processed in a steaming atmosphere at 510° C. for 30 minutes. Next, the thus-steamed product was suspended in 2000 g of pure water, to which was gradually added 32 g of 25 mas. % sulfuric acid, and stirred at 95° C. for 30 minutes, then filtered and washed. Further, the product that had been filtered and washed in that manner was suspended in 2000 g of pure water, to which was added 180 g of an aqueous solution of 1.71 mas. % tetrammine chloride-platinum, and stirred at 60° C. for 30 minutes, then filtered and washed. The resulting product that had been filtered and washed in that manner was dried overnight at 110° C., and then ground to obtain a Pt-carrying La-containing USY zeolite catalyst having a platinum content of 0.87% by mass.

(2) Production of Adamantane:

A stainless reactor tube having an inner diameter of 14 mm was filled with 20 g of the Pt-carrying La-containing USY zeolite catalyst that had been prepared in the above (1), which was then baked in air at 300° C. for 3 hours. Next, the reaction system was purged with nitrogen gas, and then subjected to hydrogen reduction in hydrogen gas under normal pressure at 300° C. for 3 hours.

Next, trimethylenenorbornane that contains 3.3% by mass of an alcohol, isopropyl alcohol was introduced into the reactor tube along with hydrogen gas thereinto, in which the trimethylenenorbornane was continuously isomerized. The reaction condition was as follows: The reaction temperature was 300° C., the reaction pressure was 5 MPa, WHSV=2.4 hr$^{-1}$, and the molar ratio of hydrogen gas to trimethylenenorbornane was 2.

50 hours after the start of the material introduction into the reactor tube, the reaction product was analyzed, and the conversion of trimethylenenorbornane and the selectivity of adamantane were calculated according to the following equations:

TMN conversion=[1−(mass of TMN after reaction)/(mass of TMN before reaction)]×100

Adamantane selectivity=[(mass of adamantane produced)/{(mass of TMN before reaction)−(mass of TMN after reaction)}]×100

In the above equations, TMN indicates trimethylenenorbornane. In this Example, the trimethylenenorbornane conversion was 81.3% by mass, and the adamantane selectivity was 17.4% by mass. The data are shown in Table 1.

COMPARATIVE EXAMPLE 1

Adamantane was produced in the same manner as in Example 1, for which, however, isopropyl alcohol was not added to the starting material trimethylenenorbornane. The data are given in Table 1.

EXAMPLE 2

Adamantane was produced in the same manner as in Example 1, for which, however, the reaction temperature was changed to 325° C. The data are given in Table 1.

COMPARATIVE EXAMPLE 2

Adamantane was produced in the same manner as in Example 2, for which, however, isopropyl alcohol was not added to the starting material trimethylenenorbornane. The data are given in Table 1.

EXAMPLE 3

Adamantane was produced in the same manner as in Example 2, for which, however, the starting material trimethylenenorbornane contained 16.7% by mass of isopropyl alcohol added thereto. The data are given in Table 1.

EXAMPLE 4

Adamantane was produced in the same manner as in Example 2, for which, however, the starting material trimethylenenorbornane contained 5% by mass of water added thereto. The data are given in Table 1.

EXAMPLE 5

Adamantane was produced in the same manner as in Example 2, for which, however, the starting material trimethylenenorbornane contained 3.3% by mass of isopropyl alcohol and 10% by mass of an unsaturated compound, benzene, added thereto. The data are given in Table 1.

EXAMPLE 6

Adamantane was produced in the same manner as in Example 2, for which, however, the starting material trimethylenenorbornane contained 3.3% by mass of isopropyl alcohol and 20% by mass of a monocyclic saturated hydrocarbon, ethylcyclohexane, added thereto. The data are given in Table 1.

EXAMPLE 7

Adamantane was produced in the same manner as in Example 2, for which, however, the starting material trimethylenenorbornane contained 3.3% by mass of isopropyl alcohol, 10% by mass of an unsaturated compound, benzene, and 20% by mass of a monocyclic saturated hydrocarbon, ethylcyclohexane, added thereto. The data are given in Table 1.

TABLE 1

| Example Comparative Example | Additive to Reaction System (mas. %) | Reaction Temperature (° C.) | TMN Conversion (%) | Adamantane Selectivity (%) |
| --- | --- | --- | --- | --- |
| Example 1 | isopropyl alcohol (3.3%) | 300 | 81.3 | 17.4 |
| Com. Ex. 1 | — | 300 | 82.2 | 13.3 |
| Example 2 | isopropyl alcohol (3.3%) | 325 | 87.1 | 18.1 |
| Com. Ex. 2 | — | 325 | 91.2 | 15.3 |
| Example 3 | isopropyl alcohol (16.7%) | 325 | 71.7 | 19.0 |
| Example 4 | water (5%) | 325 | 69.2 | 21.2 |
| Example 5 | isopropyl alcohol (3.3%) benzene (10%) | 325 | 76.0 | 20.8 |

TABLE 1-continued

| Example Comparative Example | Additive to Reaction System (mas. %) | Reaction Temperature (° C.) | TMN Conversion (%) | Adamantane Selectivity (%) |
|---|---|---|---|---|
| Example 6 | isopropyl alcohol (3.3%) ethylcyclohexane (20%) | 325 | 97.0 | 17.9 |
| Example 7 | isopropyl alcohol (3.3%) benzene (10%) ethylcyclohexane (29%) | 325 | 92.1 | 21.5 |

TMN: trimethylenenorbornane

INDUSTRIAL APPLICABILITY

In the present invention, any corrosive substance such as hydrogen chloride is not used. According to the invention, therefore, adamantanes can be selectively produced in a production apparatus made of an inexpensive material, not having any negative influence on the natural environment.

The invention claimed is:

1. A method for producing adamantanes by isomerizing a tricyclic saturated hydrocarbon having at least 10 carbon atoms in the presence of a metal-carrying solid acid catalyst, wherein water and/or alcohol is made to coexist along with the catalyst during the isomerization.

2. The method for producing adamantanes as claimed in claim 1, wherein the metal of the metal-carrying solid acid catalyst is a metal of Groups 8 to 10 of the Periodic Table.

3. The method for producing adamantanes as claimed in claim 2, wherein the metal of Groups 8 to 10 of the Periodic Table is platinum.

4. The method for producing adamantanes as claimed in claim 2, wherein the metal-carrying solid acid catalyst is a catalyst of a metal of Groups 8 to 10 of the Periodic Table supported on a zeolite.

5. The method for producing adamantanes as claimed in claim 1, wherein the metal-carrying solid acid catalyst is a solid acid catalyst of platinum supported on a Y-type zeolite.

6. The method for producing adamantanes as claimed in claim 1, wherein the isomerization reaction occurs in the additional presence of an unsaturated bond containing compound.

7. The method for producing adamantanes as claimed in claim 6, wherein said unsaturated bond-containing compound is a monocyclic saturated hydrocarbon.

8. The method for producing adamantanes as claimed in claim 6, wherein the isomerization reaction occurs in the additional presence of a monocyclic saturated hydrocarbon.

9. A method for producing adamantanes, comprising:
    isomerizing a tricyclic saturated hydrocarbon having at least 10 carbon atoms, as the tricyclic saturated hydrocarbon having water and/or alcohol mixed therewith contacts a Group 8 to 10 metal-carrying solid acid catalyst.

10. The method for producing adamantanes as claimed in claim 1, wherein the tricyclic saturated hydrocarbon having at least 10 carbon atoms is a compound selected from the group consisting of trimethylenenorbornane [tetrahydrodicyclopentadiene], perhydroacenaphthene, perhydrofluoren, perhydrophenalene, 1,2-cyclopentanperhydronaphthalene, perhydroanthracene and perhydrophenanthrene.

11. The method for producing adamantanes as claimed in claim 1, wherein the metal of the metal-carrying solid acid catalyst selected from the group consisting of iron, cobalt, nickel, ruthenium, rhodium, palladium, osmium, iridium and platinum.

12. The method for producing adamantanes as claimed in claim 4, wherein said zeolite is a member selected from the group consisting of A-type zeolite, L-type zeolite, X-type zeolite, Y-type zeolite and ZSM-5.

13. The method for producing adamantanes as claimed in claim 1, wherein the amount of water and/or alcohol is mixed with the tricyclic saturated hydrocarbon in a ratio ranging from 1:10000 and 2:1 by weight.

14. The method for producing adamantanes as claimed in claim 13, wherein said ratio ranges from 1:1000 and 1:1.

* * * * *